United States Patent [19]

Brief

[11] Patent Number: 4,747,395
[45] Date of Patent: May 31, 1988

[54] SURGICAL RETRACTOR FOR BONE SURGERY

[76] Inventor: L. Paul Brief, 18 Rockford Dr., West Nyack, N.Y. 10994

[21] Appl. No.: 526,029

[22] Filed: Aug. 24, 1983

[51] Int. Cl.⁴ .............................................. A61B 17/02
[52] U.S. Cl. ..................................................... 128/20
[58] Field of Search ........................... 128/20, 341–345

[56] References Cited

U.S. PATENT DOCUMENTS

| | | | |
|---|---|---|---|
| 2,450,194 | 9/1948 | Glaser | 128/20 |
| 2,693,795 | 11/1954 | Griesheber | 128/20 |
| 2,695,607 | 11/1954 | Hipps et al. | 128/20 |
| 3,227,156 | 1/1966 | Gauthier | 128/20 |
| 3,701,348 | 10/1972 | Nawara | 128/20 |
| 3,731,673 | 5/1973 | Halloran | 128/20 |
| 3,749,088 | 7/1973 | Gauthier | 128/20 |
| 4,259,068 | 3/1981 | Stephens | 128/20 |
| 4,344,420 | 8/1982 | Forder | 128/20 |
| 4,355,631 | 10/1982 | LeVahn | 128/20 |

Primary Examiner—Max Hindenburg
Attorney, Agent, or Firm—Helfgott & Karas

[57] ABSTRACT

The present invention relates to a surgical retractor for use in surgery of large bones, and in particular, the femur.

9 Claims, 3 Drawing Sheets

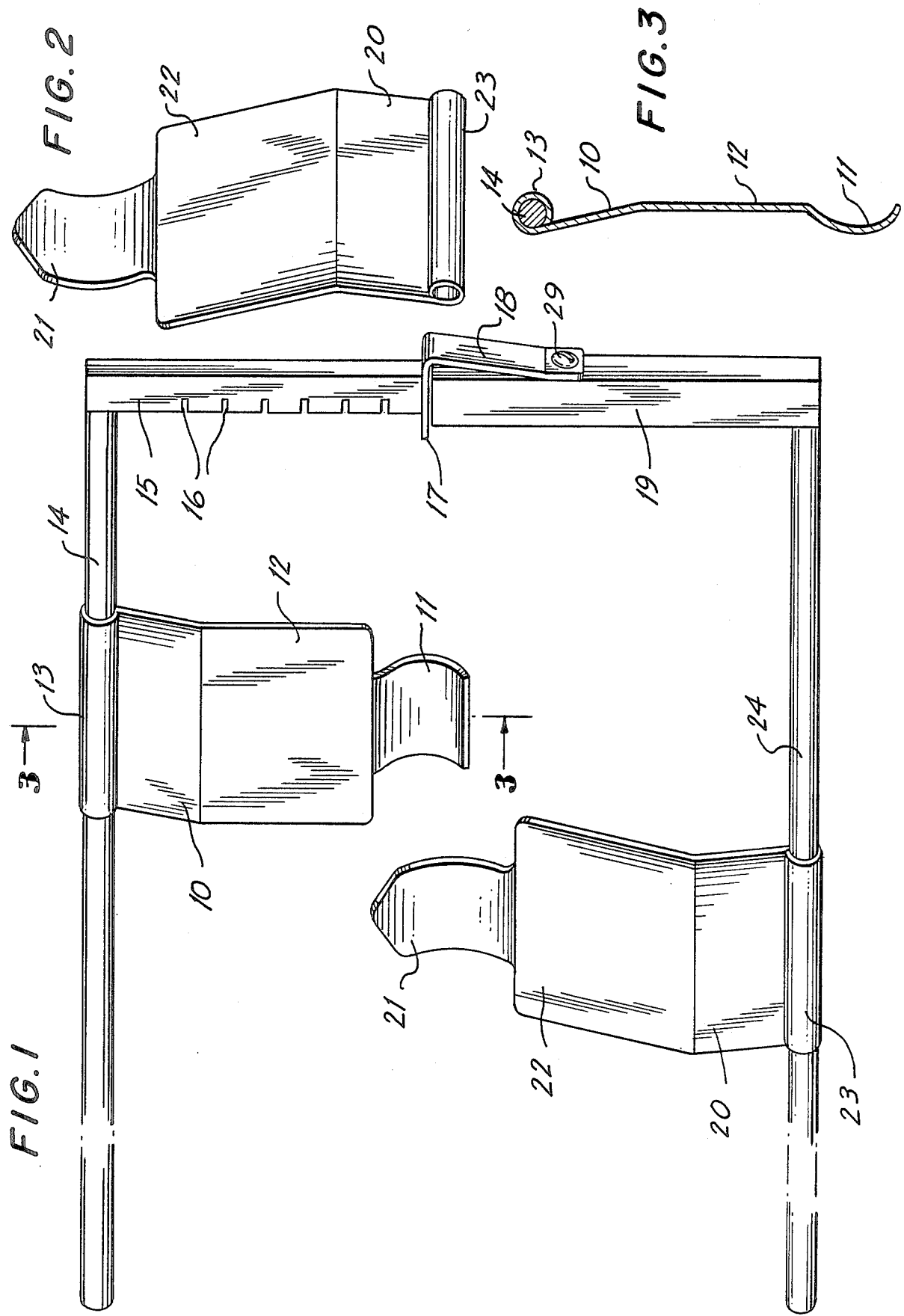

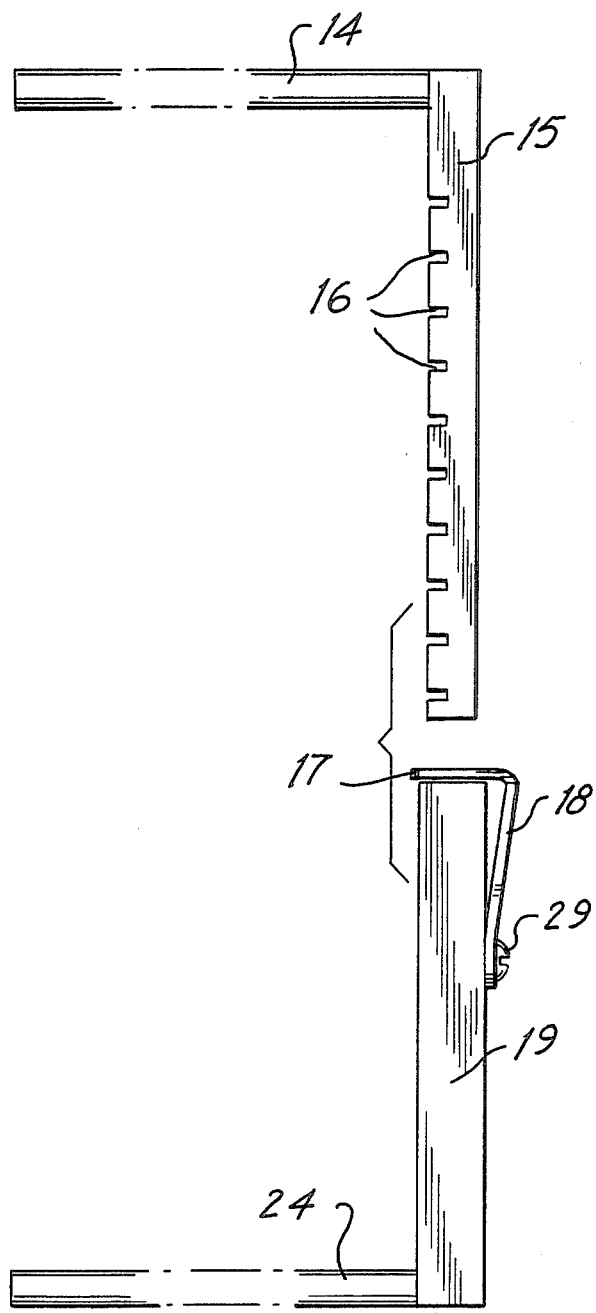
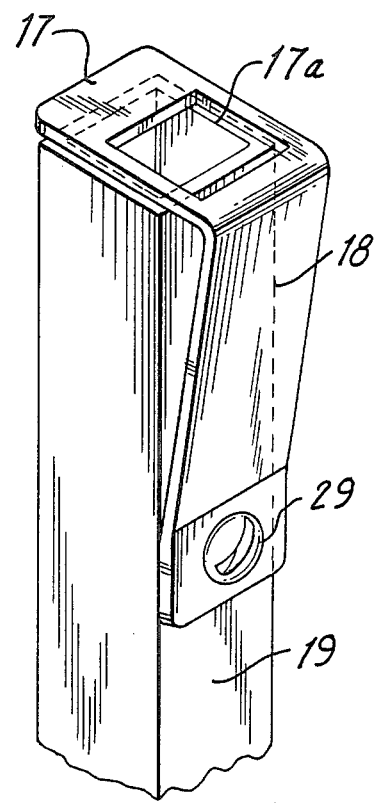

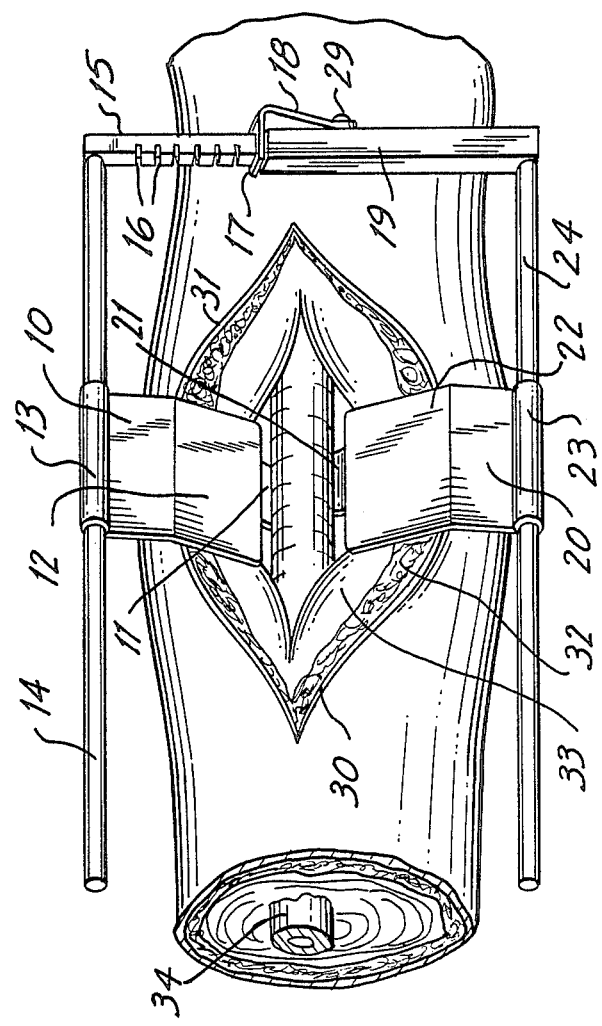
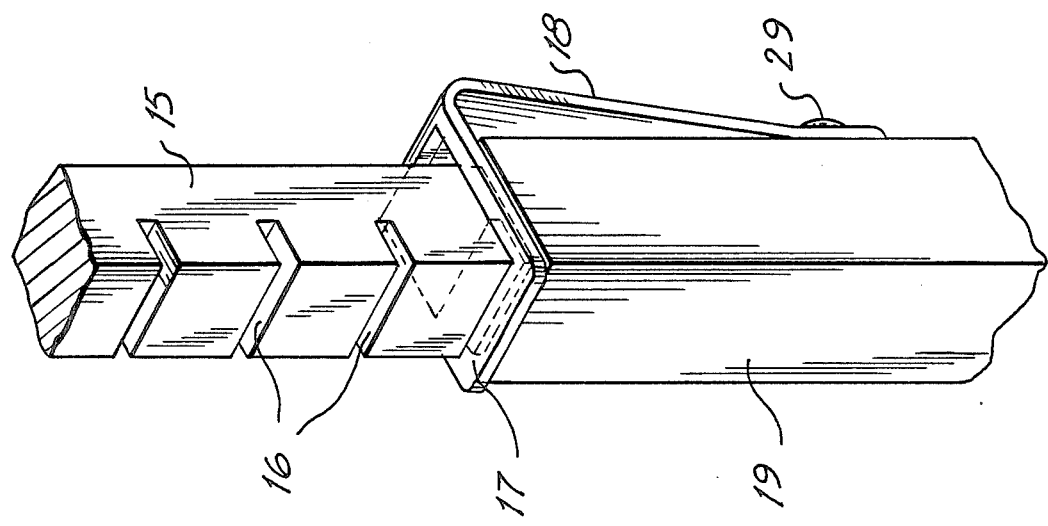

SURGICAL RETRACTOR FOR BONE SURGERY

This invention relates to a surgical retractor particularly suitable for use in displacing muscle and other non-skeletal tissue so as to provide convenient access to a femur upon which surgery is to be performed.

The normal procedure in modern operating rooms is to have a number of surgical assistants present during an operation to provide the surgeon with whatever assistance or instruments he requires. In most surgery, including surgery involving bones, the operating field is rather small, thereby necessitating providing the surgeon with the largest, unobstructed field possible to permit maximum access to the site.

One long term, partial solution to providing the surgeon with greater access to the surgical site has been the use of surgical retractors. In surgery of bone tissue, retractors have been described in the prior art which either include a pair of arms having interconnecting ends whereby the arms may be inserted in an incision, extended along opposite sides of a bone, then spread apart and the incision opened; or a pair of arms having a brace pivotally connected between the two arms to hold them apart when they are spread, thereby holding the incision open.

Muscle retractors of the former type suffer the disadvantage of requiring the surgical stripping of non-skeletal tissue from the underside of the bone to permit the two halves of the interconnected arms to be coupled together, which increases the amount of bleeding, surgical time and work required. Typical of this type of retractor is that disclosed in U.S. Pat. No. 2,695,607 where the retractors are maintained in a spread or open position by wrapping a chain fastened to the upper end of one member of the pair of retractors around the underside of the limb having the surgical site and fastening it to the upper end of the other member of the pair of retractors. Although retractors of this type provide the surgeon with an open surgical site, they can only be employed in surgery involving bones in the extremities and do require manipulation of the limb or extremity before and after surgery to attach and detach the chain.

Muscle retractors of the latter type, while avoiding the unnecessary additional surgery to utilize the retractors, do not provide the surgeon with total access to the surgical site. Instead, the brace extends between the two retractors and generally across the middle of the operative site, partially obstructing the surgeon's view and access to that site. Typical of this type of retractor is that described in U.S. Pat. No. 3,371,673.

In surgery of the femur and hip, the leg is generally maintained under traction and suspended above the operating table. Placement of the retractors is of the utmost importance since the site frequently must be X-rayed as the surgery progresses to insure proper bone relocation or hip nail placement. Accordingly, the retractor in use must be outside of the field when X-raying a hip fracture.

It is an object of the present invention to provide a surgical retractor for bone surgery which reduces the amount of bone stripping heretofore required with prior art retractors.

It is a further object of the present invention to provide a surgical retractor for bone surgery which enables the surgeon to work in a surgical field unobstructed by retractors or retractor braces.

It is yet a further object of the present invention to provide a surgical retractor for bone surgery which is simple in construction, readily sanitizable and sterilizable and is non-reactive with body tissues.

It is still a further object of this invention to eliminate the need for the surgical assistant to hold retractors during the entire surgical procedure, thus enabling the assistant to help the surgeon in other, more useful tasks, such as assembling surgical instruments, hemostasis, wound irrigation and the like.

Other objects and advantages of the present invention will become readily apparent from a further reading of the following detailed description taken in conjunction with the accompanying drawings.

SUMMARY OF THE INVENTION

The present invention is a surgical retractor, particularly suitable for use in bone surgery comprising a pair of retractor members, each having a lower bone engaging end, a central non-skeletal tissue engaging section and an upper lever arm section. The upper section of each member is adapted to receive one leg of an offset, adjustable "U" shaped expander (hereafter referred to as expander), which, when both ends are inserted into the ends of the retractor members adapted to receive such ends, maintains the upper end of the retractor members in an open or spread position, thereby moving non-skeletal tissue away from the operating site.

The surgical retractor of the present invention is eminently suitable for use in hip surgery. Most incisions for hip surgery are 6 to 8 inches long and require the use of retractors held by a surgeon's assistant. Prior art retractors such as heretofore described were not designed for hip surgery. Generally such retractors are not satisfactory for hip surgery as they are designed for use in a horizontal position rather than the vertical position required in hip surgery. When used in the vertical position, such prior art retractors are not stable and require that an assistant hold them to prevent shifting or movement in the incision during the operation.

The surgical hip retractor of the present invention is held in place solely by tension of the tissues and does not need to be held by a surgical assistant.

Furthermore, the hip retractor of the present invention permits X-raying of the hip during various stages of the surgery and nail placement and penetration without appearing in the X-ray field.

Preferably, the retractor members and expander are constructed of stainless steel, although if desired, they may be constructed of other suitable metals, such as Vitalium (a chromium-cobalt alloy) or metals covered with an elastomer covering such as dimethyl polysiloxane polymer capable of being organo-metallically bonded or otherwise affixed thereto. Dimethyl polysiloxane polymer is known for its chemical inertness, compatibility with cell metabolism and ability to withstand repeated sterilization.

The degree to which the surgeon wishes to open the operating site for access to a bone can readily be adjusted by merely increasing or decreasing the width of the expander which is inserted into the receivers on the upper ends of the pair of retractor blades. As the width of the expander is increased, the width of the surgical site is increased.

The expander is preferably constructed of rectangular configuration to avoid rotation and in two sections, each having a leg and a body member, the body member of one section having a female member adapted to slidably receive the male body member of the other section, which body member may be either solid or hollow. The female member has a releasable locking member adapted to engage and lock the male member in a fixed, predetermined position to permit the legs of the respective sections to be maintained parallel to each other in a fixed position and extending away from the body members.

When inserted into the expander leg receivers located on the upper ends of the retractor members, the legs may be further secured therein if desired, to avoid accidental shifting or slipping by providing leg locking means of a design well known to those skilled in the art, such as lock pins and the like.

DESCRIPTION OF THE DRAWINGS

FIG. 1 is a top plane view of the muscle retractor of the present invention.

FIG. 2 is a perspective view of the lower expander blade member of the present invention.

FIG. 3 is a cross-sectional view of retractor blade member 20 taken along line 3—3 in FIG. 1.

FIG. 4 is a perspective view of the two part expander of the present invention.

FIG. 5 is a partial sectional view of female expander body member showing the safety lock blade in position.

FIG. 6 is a partial sectional perspective view of male expander body member locked in position within female expander body member 19.

FIG. 7 is a transverse sectional view of a limb with the retractor of the present invention in place and holding an incision open.

DESCRIPTION OF THE PREFERRED EMBODIMENTS

As shown in FIGS. 1, 2 and 3, the surgical retractor of the present invention consists of an upper retractor blade member 10 and a lower retractor member 20, each having a bone engaging lip, 11 and 21, respectively, a central body, 12 and 22 respectively, and an upper lip, 13 and 23 respectively, said upper lip being adapated to receive expander legs 14 and 24. Expander leg 14 is rigidly fastened to male expander body member 15. Expander body member 15 is provided with a series of parallel detents 16 evenly spaced at predetermined locations on said member and adapted to receive safety lock blade 17 which forms a part of and is activated by lock control 18. Lock control 18 is attached to the upper part of female expander body member 19 by fastener means 29, typically screw or rivet means or the like. Expander leg 24 is rigidly fastened to female expander body member 19. Female expander body member 19 is adapted to receive body member 15. Body member 15 is held in position by safety lock blade 17.

As shown in FIG. 7, lower bone engaging lips 11 and 21 of retractor blade members 10 and 20 are inserted into an elongated incision 30 and engage opposite sides of the injured bone 34. Retractor blade members 10 and 20 are then pushed apart to retract the skin 31, the subcutaneous tissue and fat 32 and the deep muscle layers 33, and expander legs 14 and 24 are inserted into upper lip receivers 13 and 23, respectively. The degree to which retractor blade members 10 and 20 are to be spread to provide maximum access to the operating site may be predetermined by the surgeon and expander members 15 and 19, then adjusted to provide for suitable spacing between expander legs 14 and 24 so as to maintain retractor blade members 10 and 20 in the preselected position.

It will be apparent that the surgical retractor of the present invention may be used for all large bone surgery, typically surgery of the humerus, tibia or femur, where maximum access to the surgical side is desired while minimizing the degree of stripping required. It has been found that the surgical retractor of the present invention is eminently suitable for hip surgery.

Preferably, the bone engaging lower portion of the retractor will be relatively narrow to minimize the amount of bone stripping required, and the central and upper portions will be substantially wider to provide better contact with and retraction of the non-skeletal tissue.

It has been found that since the muscle tissues above the femur in the area of the operating field are relatively soft and the muscle tissues below the femur are relatively hard, it is preferred that the front edge of bone engaging retractor 20 of the lower lip 21 is somewhat pointed and has a beveled edge. This configuration has been found to facilitate penetration of the muscle tissue below the bone with a minimum amount of muscle stripping.

In a preferred embodiment of the present invention, the surgical retractor which is eminently suitable for hip surgery is constructed of stainless steel and has upper and lower retractor blade members 10 and 20, which have an overall width of about 2 ½ inches, a length of about 6 inches and a thickness of about 1/16 inch. Bone engaging lips 11 and 21 are preferably about 1 ¼ inches wide and about 2 inches long and have a radius approximately the same as that of the femur which they engage, i.e., about ⅜ inch. For optimum results, it is preferred that the lower retractor blade 21 be ⅛ inch longer than the upper retractor blade 11. The expander legs 14 and 24 are rods, about 12 inches long and are rigidly fastened at right angles to male expander body 15 and female expander body 19, respectively. Male expander body 15 is about 6" long and is constructed of ⅜ inch square stock with detents spaced every ½ inch along the side facing the surgical site. Female expander body member 19 is about 6 inches long and is constructed of hollow square stock with inside dimensions sufficient to receive male member 15. Female expander body member 19 has safety lock blade 17 attached to overlay the upper opening. Lock blade 17 forms part of lock control 18, which is attached to female expander body member 17 by screw means 29.

In use, after the surgeon has prepared the surgical site and stripped tissue to the degree required, upper and lower retractor blade members 10 and 20 respectively are inserted by engaging the bone 34 with upper and lower bone engaging lips 11 and 21, respectively. Male expander body member 15 is inserted into female expander body member 19 by pushing lock control 18 towards the female body member and sliding male expander body member 15 through the center 17a of lock blade 17 and into female expander body member 19. When the distance between expander legs 14 and 24 is approximately that desired by the surgeon, lock control 18 is released so that lock blade 17 can engage the nearest detent 16 merely by slightly moving male expander body member 15. Expander legs 14 and 24 can then be inserted into upper lip receivers 13 and 23, respectively. At this point the surgeon can make a final adjustment for optimum tissue retraction merely by moving expander legs 14 and 24 closer together or farther apart by the aforementioned procedures.

While the present invention has been described by means of the foregoing embodiments, reference is to be had to the appended claims for a definition of the scope of the invention.

What is claimed is:

1. A surgical retractor for bone surgery capable of being used in a vertical position during surgery comprising a pair of retractor members, each having a single element bone engaging lower section, a central, non-skeletal tissue engaging section and an upper, lever arm section; an adjustable "U" shaped expander having a pair of parallel legs attached at substantially right angles to opposite ends of an adjustable expander body section, said expander body in use having an axis parallel to the axis of the said pair of retractor members, said upper lever arm sections of said retractor having means for receiving said expander legs and enabling rotation thereon as said expander legs are moved toward or away from each other.

2. A surgical retractor for bone surgery according to claim 1 wherein said central, non-skeletal tissue engaging section and said upper, lever arm section are of substantially the same width and wider than said bone engaging lower section.

3. A surgical retractor for bone surgery according to claim 1 wherein said expander body is substantially square in configuration and said expander legs have a circular cross-section.

4. A surgical retractor for bone surgery according to claim 1 wherein said expander body has two components, male component and a female component, said female component being constructed so as to slidably receive said male component.

5. A surgical retractor for bone surgery according to claim 4 wherein said male component of said expander body is provided with equally spaced detents along its length which are of a size sufficient to receive and engage locking means which form part of said female expander member, thereby locking said two components and preventing any substantial movement of said expander legs relative to each other.

6. A surgical retractor for bone surgery according to claim 2 wherein said upper, lever arm section is adapted to rotatably receive adjustable expander legs.

7. A surgical retractor for bone surgery according to claim 1 wherein said retractor is constructed of stainless steel.

8. A surgical retractor for bone surgery according to claim 7 wherein said retractor members are about 2 ½ inches wide, about 6 inches long and about 1/16 inch thick; the bone engaging lips of said retractor members being about 2 inches long and 1 ¼ inches wide; and the male and female expander body is constructed of ⅜ inch stock and is about 6 inches long with rigidly attached legs having a length of 12 inches, said male expander body having spaced detents every ½ inch.

9. A surgical retractor according to claim 1, wherein the bone engaging lower section of the retractor which engages the lower side of the bone has a front edge which is pointed and beveled.

* * * * *